United States Patent
Dreher et al.

(10) Patent No.: US 7,077,871 B2
(45) Date of Patent: Jul. 18, 2006

(54) COLORING COMPOSITION FOR KERATIN FIBRES COMPRISING A SYSTEM LIMITING THE TRANSCUTANEOUS PASSAGE OF AN OXIDATION DYE

(75) Inventors: Frank Dreher, Paris (FR); Francis Pruche, Senlis (FR)

(73) Assignee: L'Oreal, Paris (FR)

(*) Notice: Subject to any disclaimer, the term of this patent is extended or adjusted under 35 U.S.C. 154(b) by 216 days.

(21) Appl. No.: 10/409,570

(22) Filed: Apr. 9, 2003

(65) Prior Publication Data
US 2004/0040097 A1    Mar. 4, 2004

Related U.S. Application Data

(60) Provisional application No. 60/372,817, filed on Apr. 17, 2002.

(30) Foreign Application Priority Data
Apr. 9, 2002    (FR) ................... 02 04427

(51) Int. Cl.
*A61K 7/13* (2006.01)

(52) U.S. Cl. ................ 8/405; 8/406; 8/407; 8/412; 8/424; 8/435; 8/594; 8/596; 8/600; 8/601; 8/628; 8/629; 132/202; 132/208; 424/70.1

(58) Field of Classification Search ........... 8/405, 8/406, 407, 410, 412, 424, 435, 594, 596, 8/600, 601, 628, 629; 132/202; 424/70.1
See application file for complete search history.

(56) References Cited

U.S. PATENT DOCUMENTS

| | | | | |
|---|---|---|---|---|
| 5,279,618 | A | 1/1994 | Prota et al. | 8/408 |
| 5,704,949 | A | 1/1998 | Prota et al. | 8/423 |
| 6,004,355 | A * | 12/1999 | Dias et al. | 8/406 |
| 6,723,136 | B1 * | 4/2004 | Pruche | 8/405 |

FOREIGN PATENT DOCUMENTS

| | | |
|---|---|---|
| EP | 0 342 034 | 11/1989 |
| EP | 0 697 210 | 2/1996 |
| EP | 1 210 931 | 6/2002 |
| FR | 2 814 943 | 4/2002 |
| GB | 2 132 642 | 7/1984 |
| JP | 01319411 | 12/1989 |

OTHER PUBLICATIONS

Database WPI; Selection Ch, Week 197901; Derwent Publications Ltd., London, GB; XP002230065 & JP 53 133641; Nov. 21, 1978.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Described is a method of reducing transcutaneous passage of an orthodiphenol oxidation dye by adding a catalytic system of Mn(II) or Zn(II) salt or oxide and at least one alkaline or alkaline earth hydrogenocarbonate to the orthodiphenol oxidation dye composition.

48 Claims, 1 Drawing Sheet

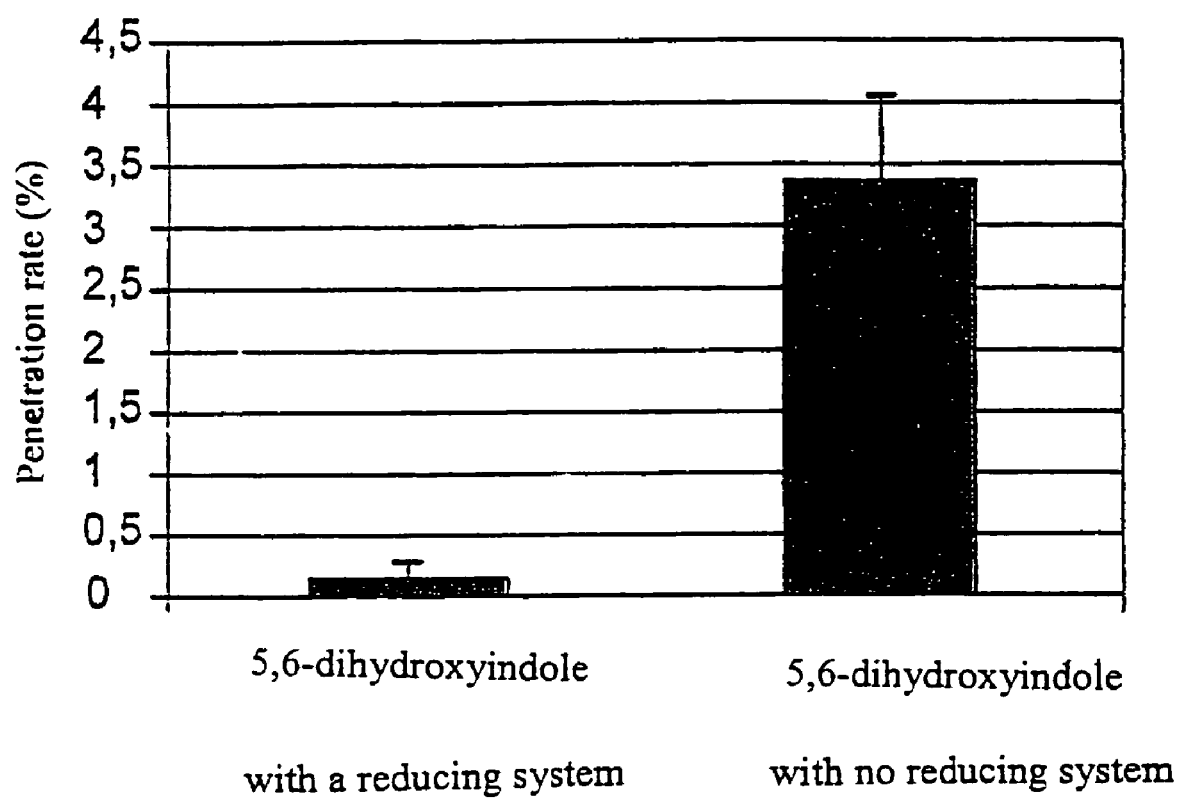

COLORING COMPOSITION FOR KERATIN FIBRES COMPRISING A SYSTEM LIMITING THE TRANSCUTANEOUS PASSAGE OF AN OXIDATION DYE

This application is based on U.S. Provisional Application No. 60/372,817, filed Apr. 17, 2002, and French Patent Application No. FR 0204427, filed Apr. 9, 2002, the entire contents of each of which are hereby incorporated by reference.

BACKGROUND OF THE INVENTION

1. Field of the Invention

The present invention generally relates to a composition for coloring the keratin fibres, leading to a better dye tolerance and the prevention of skin staining.

2. Discussion of the Background

Some oxidation dyes are likely to cause incomfort, irritatation, sensitization or hair scalp staining reactions, even if all the precautions are taken during a coloring operation in order to prevent any contact with the skin, that any possibility of contact with the skin is very short and that they are rinsed just after a coloring operation. Such intolerance reactions are likely to appear when the dye reaches the cutaneous barrier.

For hair dyes likely to cause such reactions, the penetration into the skin, though reduced, could be further limited, which would result in a better dye tolerance and would allow for skin staining to be prevented.

Numerous compound families are known having the property of activating the penetration into the skin or the keratin fibres of an active agent contained in a cosmetic and/or pharmaceutical composition.

On the other hand, very few compound families are known having the opposite activity, i.e. efficiently reducing the penetration of an active agent of a cosmetic and/or pharmaceutical composition into the skin and/or the keratin fibres.

Numerous improvements have been made in the field of cosmetic compositions for coloring the keratin fibres, and the commercially available oxidation dyes are safe. However, it would be desirable to make available an agent which, when used with a cosmetic composition for coloring keratin fibres, for example hair, would have properties of reduced penetration into the skin of the oxidation dye, without being detrimental to the keratin fibre coloration.

The present invention precisely aims at meeting such a need.

SUMMARY OF THE INVENTION

One embodiment of the present invention provides a composition, which includes:

a physiologically acceptable medium, at least one orthodiphenol oxidation dye, at least one first component selected from the group including Mn(II) salt, Mn(II) oxide, Zn(II) salt, Zn(II) oxide, and combinations thereof, and at least one second component selected from the group including alkaline hydrogencarbonate, alkaline earth hydrogencarbonate, and mixtures thereof, wherein at least one of the following equations are satisfied:

$$\frac{[Mn(II)]}{[HCO_3]} \leq 1 \text{ avec } [Mn(II)] \neq 0$$

$$\frac{[Zn(II)]}{[HCO_3]} \leq 1 \text{ avec } [Zn(II)] \neq 0$$

$$\frac{[Mn(II) + Zn(II)]}{[HCO_3]} \leq 1 \text{ avec } [Mn(II)] \text{ et } [Zn(II)] \neq 0$$

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

wherein [Mn(II)], [Zn(II)] and [HCO$_3$] respectively represent the molar concentrations of Mn(II), Zn(II) and HCO$_3$ in the composition.

Another embodiment of the invention provides a method, which includes contacting the above composition with at least one keratin fiber.

Another embodiment of the invention provides a method for making the above composition, which includes contacting:

the physiologically acceptable medium,
the least one orthodiphenol oxidation dye,
the first component, and
the second component.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein FIG. 1 shows the results of the mixtures containing 5,6-dihydroxyindole at a final concentration of 5 mM.

DESCRIPTION OF THE PREFERRED EMBODIMENTS

Various other objects, features and attendant advantages of the present invention will be more fully appreciated as the same becomes better understood from the following detailed description of the preferred embodiments of the invention.

Applicant has surprisingly discovered that a system comprising at least one manganse (II) and/or zinc (II) salt and/or oxide and an alkaline and/or alkaline earth hydrogenocarbonate has properties of reduced penetration into the skin of oxidation dyes when added to coloring compositions of the keratin fibres containing such oxidation dyes.

The composition for coloring the keratin fibres according to the invention comprises, in a physiologically acceptable medium, an effective amount of at least one orthodiphenol oxidation dye and an effective amount of a system limiting the transcutaneous passage of the oxidation dye, comprising a first component selected amongst Mn(II) and/or Zn(II) salts and oxides and a second component selected amongst alkaline hydrogenocarbonates, alkaline earth hydrogenocarbonates and the mixtures thereof, the proportions of the first component and the second component being such that:

where [Mn(II)], [Zn(II)] and [HCO$_3$] respectively represent the molar concentrations of Mn(II), Zn(II) and HCO$_3$ in the composition, Generally, the $$\frac{[Mn(II)]}{[HCO_3]}$$

ratio ranges from $10^{-5}$ to $10^{-1}$, preferably from $10^{-3}$ to $10^{-2}$ and typically in the order of $5.10^{-3}$. This ratio includes 1, 2, 3, 4, 5, 6, 7, 8, and $9 \times 10^{-5}$, 1, 2, 3, 4, 5, 6, 7, 8, and $9 \times 10^{-4}$, 1, 2, 3, 4, 5, 6, 7, 8, and $9 \times 10^{-3}$, 1, 2, 3, 4, 5, 6, 7, 8, and $9 \times 10^{-2}$, and 1, 2, 3, 4, 5, 6, 7, 8, and $9 \times 10^{-1}$.

In the case of Zn(II), the $$\frac{[Zn(II)]}{[HCO_3]}$$

ratio is generally of an order from 10 to 100 times higher than the ratio in the case of Mn(II). This range includes 20, 30, 40, 50, 60, 70, 80, and 90 times.

Typically, such a ratio is $10^{-4}$ or higher, preferably $10^{-3}$ or higher, and preferably in the order of $5.10^{-1}$.

In the case of a mixture of Mn(II) and Zn(II), the ratio generally ranges from $10^{-5}$ to $10^{-1}$, preferably from $10^{-3}$ to $10^{-2}$, such a ratio being selected higher when the Zn(II) proportion in the mixture is increased. This ratio includes 1, 2, 3, 4, 5, 6, 7, 8, and $9 \times 10^{-5}$, 1, 2, 3, 4, 5, 6, 7, 8, and $9 \times 10^{-4}$, 1, 2, 3, 4, 5, 6, 7, 8, and $9 \times 10^{-3}$, 1, 2, 3, 4, 5, 6, 7, 8, and $9 \times 10^{-2}$, and 1, 2, 3, 4, 5, 6, 7, 8, and $9 \times 10^{-1}$.

Generally, the molar concentration of Mn(II), Zn(II) or Mn(II)+Zn(II) in the final composition ranges from $10^{-3}$ to 10 mM/l, preferably from $10^{-2}$ to 1 mM/l. This ratio includes 1, 2, 3, 4, 5, 6, 7, 8, and $9 \times 10^{-3}$, 1, 2, 3, 4, 5, 6, 7, 8, and $9 \times 10^{-2}$, 1, 2, 3, 4, 5, 6, 7, 8, and $9 \times 10^{-1}$, and 1, 2, 3, 4, 5, 6, 7, 8, and 9 mM/l.

When only one or more Mn(II) salts or oxides are being used, the Mn(II) molar concentration in the final composition can be selected in a range from $10^{-3}$ to $10^{-1}$ mM/l, preferably from $10^{-2}$ to $10^{-1}$ mM/l. This ratio includes 1, 2, 3, 4, 5, 6, 7, 8, and $9 \times 10^{-3}$, 1, 2, 3, 4, 5, 6, 7, 8, and $9 \times 10^{-2}$, 1, 2, 3, 4, 5, 6, 7, 8, and $9 \times 10^{-1}$, and 1, 2, 3, 4, 5, 6, 7, 8, and 9 mM/l.

Preferably, when only one or more Zn(II) salts or oxides are being used, the Zn(II) concentration in the final composition ranges from $5.10^{-2}$ to 10 mM/l, preferably from $5.10^{-1}$ to 1 mM/l. This ratio includes 5, 6, 7, 8, and $9 \times 10^{-2}$, 1, 2, 3, 4, 5, 6, 7, 8, and $9 \times 10^{-1}$, and 1.

Mn(II) and Zn(II) salts suitable for the present invention include chloride, fluoride, iodide, sulfate, phosphate, nitrate and perchlorate, carboxylic acid salts and the mixtures thereof.

As an example, manganese chloride, manganese carbonate (for example rhodochrosite), Mn(II) difluoride, Mn(II) acetate tetrahydrate, Mn(II) lactate trihydrate, Mn(II) phosphate, Mn(II) iodide, Mn(II) nitrate trihydrate, Mn(II) bromide, Mn(II) perchlorate tetrahydrate and Mn(II) sulphate monohydrate may be mentioned.

The most preferred salts are MnCl$_2$ and ZnCl$_2$, more particularly MnCl$_2$.

Carboxylic acid salts also include hydroxylated carboxylic acid salts such as gluconate.

Alkaline and alkaline earth hydrogenocarbonates include Na, K, Mg, Ca hydrogenocarbonates and the mixtures thereof, more particularly the Na hydrogenocarbonate.

Generally, the oxidation dyes of the compositions according to the invention are each compounds or compound mixtures which, in the presence of oxygen, for example oxygen from the air, get oxidized so as to yield a colored compound or compound mixture.

The orthodiphenol oxidation dyes are compounds comprising at least one aromatic cycle, at least two consecutive carbons of which bear a hydroxyl group. Preferably, the aromatic ring is a benzene ring or a condensed aromatic ring.

The aromatic ring may be a condensed aromatic ring optionally containing one or more heteroatoms, such as naphthalene, tetrahydronaphthalene, indane, indene, anthracene, phenanthrene, indole, isoindole, indolin, isoindolin, benzofuran, dihydrobenzofuran, chroman, isochroman, chromene, isochromene, quinoline, tetrahydroquinoline and isoquinoline.

The preferred orthodiphenol oxidation dyes may be represented by the formula:

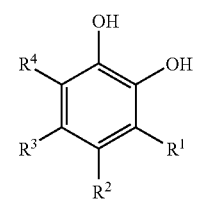

(I)

where the R$^1$ to R$^4$ substituents are identical or different and represent a hydrogen atom, a halogen, hydroxyl, carboxyl, alkyl carboxylate, optionally substituted amino, linear or branched optionally substituted alkyl, linear or branched optionally substituted alkenyl, optionally substituted cycloalkyl, alkoxy, alkoxyalkyl, alkoxyaryl, the aryl group optionally being substituted, aryl, substituted aryl and optionally substituted heterocyclic moiety, a moiety containing one or more silicon atoms, wherein two of the R$^1$ to R$^4$ substituents form together a saturated or unsaturated ring optionally containing one or more heteroatoms or optionally condensed with one or more saturated or unsaturated rings optionally containing one or more heteroatoms.

The saturated or unsaturated rings, optionally condensed, may also optionally be substituted.

The alkyl moieties are generally C$_2$–C$_{10}$ alkyl moieties, preferably C$_1$–C$_6$ alkyl moieties, such as methyl, ethyl, propyl, butyl, pentyl and hexyl.

The alkoxy moieties are generally C$_1$–C$_{20}$ alkoxy moieties, such as methoxy, ethoxy, propoxy and butoxy.

The alkyl alkoxy moieties are preferably (C$_1$–C$_{20}$)alkoxy (C$_1$–C$_{20}$)alkyl moieties, such as methoxymethyl, ethoxymethyl, methoxyethyl, ethoxyethyl, etc.

The cycloalkyl moieties are generally C$_4$–C$_8$ cycloalkyl moieties, preferably cyclopentyl and cyclohexyl moieties. The cycloalkyl moieties may be cycloalkyl moieties substituted in particular by alkyl, alkoxy, carboxylic acid, hydroxyl, amine and ketone groups.

The alkenyl moieties are preferably C$_2$–C$_{20}$ moieties such as ethylene, propylene, butylene, pentylene, methyl-2-propylene and decylene.

The moieties containing one or more silicon atoms are preferably polydimethylsiloxane, polydiphenylsiloxane, polydimethylphenylsiloxane and stearoxydimethicone moieties.

Heterocyclic moieties are generally moieties comprising one or more heteroatoms selected amongst O, N and S, preferably O or N, optionally substituted by one or more alkyl, alkoxy, carboxylic acid, hydroxyl, amine or ketone groups.

Preferred heterocyclic moieties include furyl, pyranyl, pyrrolyl, imidazolyl, pyrazolyl, pyridyl and thienyl groups.

More preferably, the heterocyclic groups are condensed groups such as benzofuranyl, chromenyl, xanthenyl, indolyl, isoindolyl, quinolyl, isoquinolyl, chromanyl, isochromanyl, indolinyl, isoindolinyl, coumarinyl and isocoumarinyl groups, such groups being optionally substituted, in particular by one or more OH groups.

The preferred orthodiphenol dyes are:
flavanols such as catechin and epichatechin gallate,
flavanols such as quercetin,
anthocyanidins such as peonidin,
anthocyanins such as oenin,
hydroxybenzoates such as gallic acid,
flavones such as luteolin,
iridoids such as oleuropein, such products being optionally osylated (for example, glucosylated) and/or being present in the form of oligomers (procyanidins);
hydroxystilbenes, for example tetrahydroxy-3,3',4,5'-stilbene, optionally osylated (for example glucosylated);
3,4-dihydroxyphenylalanine and the derivates thereof;
2,3-dihydroxyphenylalanine and the derivates thereof;
4,5-dihydroxyphenylalanine and the derivates thereof;
4,5-dihydroxyindole and the derivates thereof;
5,6-dihydroxyindole and the derivates thereof;
6,7-dihydroxyindole and the derivates thereof;
2,3-dihydroxyindole and the derivates thereof;
dihydroxycinnamates such as cafeic acid and chlorogenic acid;
hydroxycoumarins;
hydroxyisocoumarins;
hydroxycoumarones;
hydroxyisocoumarones;
hydroxychalcones;
hydroxychromones;
anthocyanines;
quinones;
hydroxyxanthones; and
the mixtures thereof.

When the dyes show D and L forms, both forms may be used in the compositions according to the invention.

Particularly preferred orthodiphenol oxidation dyes are 5,6-dihydroxyindole and 5,6-dihydroxyindolecarboxylic acid.

The polymers formed particularly with catechin, gallic acid and the derivates thereof (tannins) have antimicrobial properties through microorganism capturing upon the polymerization step.

The orthodiphenol oxidation dyes may be contained in plant, fruit, citrus, vegetable extracts or mixtures of such extracts.

The plant extracts include rose and tea extracts.

The fruit extracts include apple, grape (particularly grape seed) and banana extracts.

The vegetable extracts include potato extract.

Mixtures of plant and/or fruit extracts such as apple and tea extract mixtures and grape and apple extract mixtures may be also used.

Depending on the fruit parts being used, for example, grape pulp or seeds, the resulting coloration is different.

The compositions according to the invention may also comprise, beside the orthodiphenol oxidation dye, at least one second oxidation dye other than the orthodiphenol dye selected amongst the para or ortho types oxidation bases, coupling agents and the mixtures thereof.

The oxidation bases are compounds which are not dyes as such, but form a dye through an oxidative condensation process, either by themselves or in the presence of a coupling or modifying agent.

The oxidation bases are compounds comprising functional groups, either two amino groups or one amino group and one hydroxy group in para or ortho position relative to one another.

The nature of such oxidation bases is not critical. They may be particularly selected amongst ortho- and para-phenylenediamines, double bases, ortho- and para-aminophenols, heterocyclic bases as well as addition salts of all such compounds with an acid.

As paraphenylenediamines, one can particularly mention para-phenylenediamines of the following formula (II) and the addition salts thereof with an acid:

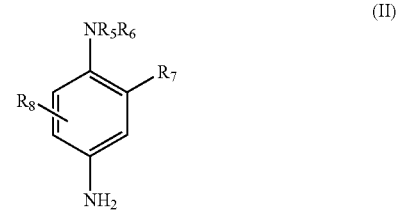

(II)

where:
$R_5$ represents a hydrogen atom, $C_1-C_4$ alkyl, $C_1-C_4$ monohydroxyalkyl, $C_2-C_4$ polyhydroxyalkyl, $(C_1-C_4)$alkoxy$(C_1-C_4)$alkyle, nitrogen-substituted $C_1-C_4$ alkyl, phenyl or 4'-aminophenyl moieties;

$R_6$ represents a hydrogen atom, $C_1-C_4$ alkyl, $C_1-C_4$ mono-hydroxyalkyl or $C_2-C_4$ polyhydroxyalkyl, $(C_1-C_4)$alkoxy$(C_1-C_4)$alkyl or nitrogen-substituted $C_1-C_4$ alkyl moieties;

$R_7$ represents a hydrogen atom, a halogen atom, such as a chlorine atom, $C_1-C_4$ alkyl, sulfo, carboxy, $C_1-C_4$ monohydroxyalkyl or $C_1-C_4$ hydroxyalkoxy, $C_1-C_4$ acetylaminoalkoxy, $C_1-C_4$ mesylaminoalkoxy or $C_1-C_4$ carbomoylaminoalkoxy moieties;

$R_8$ represents a hydrogen, a halogen atom or a $C_1-C_4$ alkyl moiety;

$R_5$ and $R_6$ may also form together with the nitrogen atom carrying them a 5 or 6 ring member nitrogen heterocycle optionally substituted by one or more alkyl, hydroxy or ureido groups.

Nitrogenous groups of the above-mentioned formula (II) include particularly amino, mono$(C_1-C_4)$alkylamino, di$(C_1-C_4)$alkylamino, tri$(C_1-C_4)$alkylamino, monohydroxy $(C_1-C_4)$alkylamino, imidazolinium and ammonium.

Paraphenylenediamines of the above-mentioned formula (II) include more particularly paraphenylenediamine, para-toluylenediamine, 2-chloroparaphenylenediamine, 2,3-dimethyl-paraphenylenediamine, 2,6-dimethylparaphenylenediamine, 2,6-diethyl-paraphenylenediamine, 2,5-dimethylparaphenylenediamine, N,N-dimethylparaphenylenediamine, N,N- diethylparaphenylenediamine, N,N-dipropyl-paraphenylenediamine, 4-amino-N,N-diethyl-3-methylaniline, N,N-bis-(β-hydroxyethyl)-paraphenylenediamine, 4-N,N-bis-(β-hydroxyethyl)amino-2-methylaniline, 4-N,N-bis-(β-hydroxyethyl)-amino-2-chloroaniline, 2-β-hydroxyethyl-para-phenylenediamine, 2-fluoro-paraphenylenediamine, 2-isopropyl-para-phenylenediamine, N-(β-hydroxypropyl)-paraphenylenediamine, 2-hydroxymethyl-paraphenylenediamine, N,N-dimethyl-3-methyl-para-phenylenediamine, N,N-(ethyl,β-hydroxyethyl)-paraphenylenediamine, N-(β,γ-dihydroxypropyl)-paraphenylenediamine, N-(4'-aminophenyl)-para-phenylenediamine, N-phenyl-paraphenylenediamine, 2-β-hydroxyethyloxy-paraphenylenediamine, 2-β-acetylaminoethyloxy-paraphenylenediamine, N-(β-methoxyethyl)-paraphenylenediamine, 2-methyl-1-N-β-hydroxyethyl-paraphenylenediamine and the addition salts thereof with an acid.

Preferred paraphenylenediamines of the above-mentioned formula (II) include more particularly paraphenylenediamine, para-toluylenediamine, 2-isopropyl-paraphenylenediamine, 2-β-hydroxy-ethyl-paraphenylenediamine, 2-β-hydroxyethyloxy-paraphenylenediamine, 2,6-dimethyl-paraphenylenediamine, 2,6-diethyl-paraphenylenediamine, 2,3-dimethyl-paraphenylenediamine, N,N-bis-(β-hydroxyethyl)-paraphenylene-diamine, 2-chloro-paraphenylenediamine and the addition salts thereof with an acid.

According to the invention, the expression double bases means compounds comprising at least two aromatic cores on which amino and /or hydroxyl groups are carried.

Double bases convenient for a use as oxidation bases in the dyeing compositions according to the invention include more particularly compounds of the following formula (III) and the addition salts thereof with an acid:

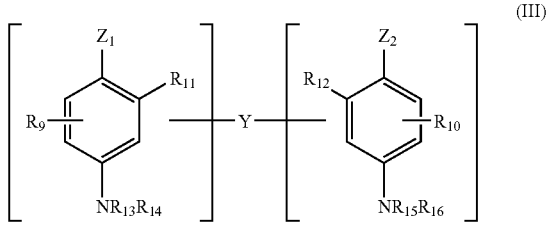

where:
Z$_1$ and Z$_2$ are identical or different and represent a hydroxyl or —NH$_2$ moiety which may be substituted by a C$_1$–C$_4$ alkyl moiety or by a linking arm Y;
the linking arm Y represents a linear or branched alkylene chain comprising from 1 to 14 carbon atoms, which may be interrupted or terminated by one or more nitrogen groups and/or by one or more heteroatoms such as oxygen, sulfur or nitrogen atoms and optionally substituted by one or more C$_1$–C$_6$ hydroxyl or alkoxy moieties;
R$_9$ and R$_{10}$ represent a hydrogen or halogen atom, C$_1$–C$_4$ alkyl, C$_1$–C$_4$ monohydroxyalkyl, C$_2$–C$_4$ polyhydroxyalkyl, C$_1$–C$_4$ aminoalkyl moieties or a linking arm Y;
R$_{11}$, R$_{12}$, R$_{13}$, R$_{14}$, R$_{15}$ and R$_{16}$ are identical or different and represent a hydrogen atom, a linking arm Y or a C$_1$–C$_4$ alkyl moiety, provided that the compounds of the formula (III) only comprise one linking arm Y per molecule.

Nitrogenous groups of the above-mentioned formula (III) include particularly amino, aminomono(C$_1$–C$_4$)alkyl, aminodi(C$_1$–C$_4$)alkyl, aminotri(C$_1$–C$_4$)alkyl, aminomono(C$_1$–C$_4$)hydroxyalkyl, imidazolinium and ammonium moieties.

Double bases of the above-mentioned formula (III) include more particularly N,N'-bis-(β-hydroxyethyl)-N,N'-bis-(4'-aminophenyl) 1,3-diaminopropanol, N,N'-bis-(β-hydroxyethyl)-N,N'-bis-(4'-amino-phenyl)ethylenediamine, N,N'-bis-(4-aminophenyl)tetramethylenediamine, N,N'-bis-(β-hydroxyethyl)-N,N'-bis-(4-aminophenyl)tetramethylenediamine, N,N'-bis-(4-methyl-aminophenyl)tetramethylenediamine, N,N'-bis-(ethyl)-N,N'-bis-(4'-amino,3'-methylphenyl)ethylenediamine, 1,8-bis-(2,5-diaminophenoxy)-3,5-dioxaoctane and the addition salts thereof with an acid.

Amongst the double bases of the formula (II), N,N'-bis-(β-hydroxyethyl)-N,N'-bis-(4'-aminophenyl)-1,3-diaminopropanol, 1,8-bis-(2,5-diaminophenoxy)-3,5-dioxaoctane or one of their addition salts with an acid are particularly preferred.

The para-aminophenols include more particularly para-aminophenols of the following formula (IV) and the addition salts thereof with an acid:

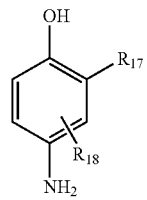

where:
R$_{17}$ represents a hydrogen atom, a halogen atom such as fluorine or chlorine, C$_1$–C$_4$ alkyl, C$_1$–C$_4$ monohydroxyalkyl, (C$_1$–C$_4$)alkoxy(C$_1$–C$_4$)alkyl or C$_1$–C$_4$ aminoalkyl or (C$_1$–C$_4$)hydroxyalkyl(C$_1$–C$_4$)aminoalkyl moieties; and
R$_{18}$ represents a hydrogen atom or a halogen atom such as fluorine or chlorine, C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alcoxy(C$_1$–C$_4$)alkyl moieties.

Para-aminophenols of the above-mentioned formula (IV) include more particularly para-aminophenol, 4-amino-3-methyl-phenol, 4-amino-3-fluoro-phenol, fluoro-phenol, 4-amino-3-hydroxymethyl-phenol, 4-amino-2-methyl-phenol, 4-amino-2-hydroxymethyl-phenol, 4-amino-2-methoxy-methyl-phenol, 4-amino-2-aminomethyl-phenol, 4-amino-2-(β-hydroxy-ethyl-aminomethyl)-phenol and the addition salts thereof with an acid.

Ortho-aminophenols useful as oxidation bases within the scope of the present invention are more particularly selected amongst 2-amino-phenol, 2-amino-1-hydroxy-5-methyl-benzene, 2-amino-1-hydroxy-6-methyl-benzene, 5-acetamido-2-amino-phenol and the addition salts thereof with an acid.

Heterocyclic bases useful as oxidation bases in the dyeing compositions according to the invention include more particularly pyridine derivates, pyrimidine derivates, pyrazole derivates and the addition salts thereof with an acid.

Pyridine derivates include more particularly the compounds disclosed for example in Patents GB-1026978 and GB-1153196, such as 2,5-diamino-pyridine, 2-(4-methoxyphenyl)amino-3-amino-pyridine, 2,3-diamino-6-methoxypyridine, 2-(β-methoxyethyl)amino-3-amino-6-methoxypyridine, 3,4-diamino-pyridine and the addition salts thereof with an acid.

Pyrimidine derivates include more particularly the compounds disclosed, for example, in German Patent DE-2359399 or Japanese JP 88-169571 and JP-9110659 or Patent Applications WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and pyrazolopyrimidine derivates such as those mentioned in Patent Application FR-A-2,750,048 and amongst which one can mention pyrazolo-[1,5-a]-pyrimidine-3,7-diamine, pyrazolo-[1,5-a]-pyrimidine-3,5-diamine, 2,7-dimethyl-pyrazolo-[1,5-a]-pyrimidine-3,5-diamine, 3-amino-pyrazolo-[1,5-a]-pyrimidin-7-ol, 3-amino-pyrazolo-[1,5-a]-pyrimidin-5-ol, 2-(3-amino pyrazolo-[1,5-a]-pyrimidin-7-ylamino) ethanol, 2-(7-amino-pyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo[1,5-a]-pyrimidin-3-yl)-(2-hydroxy-ethyl)-amino] ethanol, 5,6-dimethyl-pyrazolo-[1,5-a]-pyrimidine-3,7-diamine, 2,6-dimethyl-pyrazolo-[1,5-a]-pyrimidine-3,7-diamine, 2,5,N7,N7-tetramethyl-pyrazolo-[1,5-a]-pyrimidine-3,7-diamine, 3-amino-5-methyl-7-imidazolylpropylaminopyrazolo-[1,5-a]-pyrimidine and the addition salts and the tautomeric forms thereof, when there is a tautomeric equilibrium, and the addition salts thereof with an acid.

Pyrazolic derivates include more particularly the compounds disclosed in Patents DE-3843892, DE-4133957 and Patent Applications WO 94/08969, WO 94/08970, FR-A-2733749 and DE-19543988, such as 4,5-diamino-1-methyl-pyrazole, 3,4-diamino-pyrazole, 4,5-diamino-1-(4'-chlorobenzyl)-pyrazole, 4,5-diamino-1,3-dimethyl-pyrazole, 4,5-diamino-3-methyl-1-phenyl-pyrazole, 4,5-diamino-1-methyl-3-phenyl-pyrazole, 4-amino-1,3-dimethyl-5-hydrazino-pyrazole, 1-benzyl-4,5-diamino-3-methyl-pyrazole, 4,5-diamino-3-tert-butyl-1-methyl-pyrazole, 4,5-diamino-1-tert-butyl-3-methyl-pyrazole, 4,5-diamino-1-(β-hydroxyethyl)-3-methyl-pyrazole, 4,5-diamino-1-(β-hydroxyethyl)-pyrazole, 4,5-diamino-1-ethyl-3-methyl-pyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methyl-pyrazole, 4,5-diamino-3-hydroxymethyl-1-isopropyl-pyrazole, 4,5-diamino-3-methyl-1-isopropyl-pyrazole, 4-amino-5-(2'-aminoethyl)-amino-1,3-dimethyl-pyrazole, 3,4,5-triamino-pyrazole, 1-methyl-3,4,5-triamino-pyrazole, 3,5-diamino-1-methyl-4-methylamino-pyrazole, 3,5-diamino-4-(β-hydroxyethyl)amino-1-methyl-pyrazole, and the addition salts thereof with an acid.

According to the present invention, the oxidation bases preferably account for from 0.0005 to 12% by weight based on the total weight of the composition, more preferably from 0.005 to 8% by weight of said weight.

The coupling agents useful in the compositions according to the invention may be selected amongst those conventionally used in oxidation dyeing, more particularly amongst meta-aminophenols, meta-phenylenediamines, meta-diphenols, naphthols and heterocyclic coupling agents such as, for example indolic derivates, indolinic derivates, sesamol and the derivates thereof, pyridinic derivates, pyrazolotriazole derivates, pyrazolones, indazoles, benzimidazoles, benzothiazoles, benzoxazoles, 1,3-benzodioxols, quinolines and the addition salts thereof with an acid, such compounds being different from the orthodihydroxylated compounds of the invention.

Such coupling agents are more particularly selected amongst 2,4-diamino-1-(β-hydroxyethyloxy)benzene, 2-methyl 5-aminophenol, 5-N-(β-hydroxyethyl)amino-2-methylphenol, 3-aminophenol, 1,3-dihydroxy benzene, 1,3-dihydroxy-2-methylbenzene, 4-chloro-1,3-dihydroxybenzene, 2-amino-4-(β-hydroxyethylamino)-1-methoxybenzene, 1,3-diamino benzene, 1,3-bis-(2,4-diaminophenoxy)propane, sesamol, 1-amino-2-methoxy-4,5-methylenedioxybenzene, α-naphtol, 6-hydroxyindole, 4-hydroxyindole, 4-hydroxy-N-methylindole, 6-hydroxyindolin, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo-[3,2-c]-1,2,4-triazole, 2,6-dimethyl-pyrazolo-[1,5-b]-1,2,4-triazole and the addition salts thereof with an acid.

Generally, the coupling agent(s) preferably account(s) for from 0.0001 to 15% by weight of the total weight of the ready-made dyeing composition, more preferably from 0.001 to 10%.

The oxidation bases and the coupling agents are oxidation dyes. The addition salts with an acid of such oxidation dyes are more particularly selected amongst hydrochlorates, hydrobromates, sulfates and tartrates, lactates and acetates.

Compositions according to the invention may additionally include one or more direct dyes, more particularly in order to modify the shades with shimmer being highlighted. Such direct dyes may in particular be selected amongst nitrogenous, azoic or anthraquinonic, neutral, cationic or anionic dyes in the weight proportion ranging from about 0.001 to 20%, preferably from 0.01 to 10% of the total weight of the composition.

Compositions according to the invention may also include an effective amount of at least one amino acid comprising particularly at least one thiol group (SH) and preferably only one thiol group, such amino acids being optionally present in the form of hydrochlorates and/or at least one protein, more particularly one peptid.

Preferred amino acids according to the invention are those amino acids containing an amine function in an α position relative to a carboxylic acid function.

Preferred amino acids may be represented by the formula:

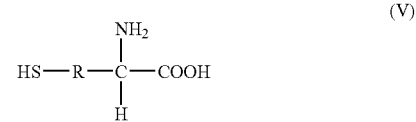

(V)

where —R is a linear or branched divalent hydrocarbon moiety, for example in $C_1$–$C_{10}$, preferably in $C_1$–$C_6$, such as methylene, ethylene, butylene, ethylidene, propylidene moieties, an optionally substituted divalent saturated cyclic moiety, for example in $C_4$–$C_8$, an optionally substituted divalent aromatic group, such as a phenylene, tolylene, xylylene moieties.

Preferred amino acids for the compositions of the invention include cysteine and the derivates thereof, particularly L-cysteine and L-cysteine hydrochlorate.

Proteins include glutathione and the derivates thereof and soja protein.

The relative proportions of amino acid and/or soja protein and oxidation dye in the compositions of the invention may vary in broad ranges depending on the desired coloration. Generally, the molar ratio amino acid/oxidation dye ranges from 0.001 to 50, preferably from 0.01 to 5 and more preferably from 0.05 to 2.5.

Generally, the content of amino acid with a thiol group in the final composition is at least 0.01 micromole per mL (µM/ml), preferably at least 0.1 µM/ml.

Varying the nature of the dye precursors and the amino acids of the compositions and the relative proportion of amino acids and dye precursor, a whole shade range can be obtained.

The compositions according to the invention may additionally comprise one or more enzymes.

The enzyme(s) present in the compositions according to the invention may be any enzymes having some propigmenting activity.

The propigmenting activity may be defined as the enzymatic activity catalyzing for the oxidation of a substrate so as to lead to the formation of pigments.

The enzymes may indeed be selected amongst pyranose oxidases, glucose oxidases, glycerol oxidases, lactate oxidases, pyruvate oxidases, uricases, choline oxidases, sarcosine oxidases, bilirubine oxidases, laccases, tyrosinases, peroxydases, catalases, superoxide dimutases and the mixtures thereof, or amongst vegetable or animal extracts containing the above-mentioned enzymes, in the optional presence of a donor (or substrate) necessary for working of said enzymes such as for example L-tyrosine or L-DOPA.

The enzymes used according to the invention may be from animal, microbiological (bacterial, fungal or viral) or synthetic (obtained through chemical or biotechnological synthesis) origin.

The enzyme(s) may be used in a pure crystallin form or in a diluted form in an inert diluent for said enzyme.

Uricase examples include particularly the uricase extracted from wild boar's liver, the *Arthrobacter globiformis uricase*, as well as the *Aspergillus flavus uricase.*

An example of choline oxidase sources includes particularly rat's liver, bacteria such as *Arthrobacter globiformis, Achromobacter cholinophagum* or *Alcaligenes*, and fungi such as *Cylindrocarpon didynum.*

An example of sarcosine oxidase sources includes particularly bacteria such as Arthrobacter and more particularly *Arthrobacter ureafaciens* and *Arthrobacter globiformis, Streptomyces, Bacillus, Pseudomonas, Corynebacterium* or *Alcaligenes*, such as for example *Alcaligenes denitrificans*, and fungi such as *Cylindrocarpon didynum.*

An example of bilirubin oxidase sources includes particularly rat's intestine mucous membrane and liver, bacteria such as *Myrothecium verucania, Myrothecium cinctum* and *Myrothecium roridum.*

Laccases from plant origin useful according to the invention include laccases produced by plants performing the chlorophylous synthesis such as indicated in Patent Application FR-A-2694018.

One can particularly mention the laccases extracted from Anacardiacea, Podocarpacea, Rosmarinus off., *Solanum tuberosum, diris* sp., *Coffea* sp., *Daucus carrota, Vinca minor, Persea americana, Catharenthus roseus, Musa* sp., *Malus pumila, Gingko biloba* and *Monotropa hypopithys* (sucepine).

Laccases from microbial origin (in particular fungal ones) or obtained through biotechnology, useful according to the invention, include *Polyporus versicolor, Rhizoctonia praticola* and rhus vernicifera laccases, such as disclosed for example in Patent Applications FR-A-2112549 and EP-A-504,005; laccases disclosed in Patent Applications WO 95/07988, WO 95/33836, WO 95/33837, WO 96/00290, WO 97/19998 and WO 97/1999, the content of which is incorporated into the present invention, as for example Scytalidium, *Polyporus pinsitus, Myceliophthora thermophila, Rhizoctonia solani, Pyricularia orizae laccases* and the variants thereof.

Laccases from microbial origin or those obtained by biotechnology will be more preferably selected.

In a particularly preferred embodiment of the invention, the enzyme being used corresponds to tyrosinase (EC 1.14.18.1 nomenclature). It is meant under tyrosinase herein any enzyme with a tyrosinase activity, such enzyme being able to show other enzyme activities. The tyrosinase activity may be defined as the enzyme activity catalyzing for the tyrosine so as to lead to the formation of the melanin precursor: Dopaquinone.

An example of tyrosinase sources includes particularly potato, fungi, microorganisms such as *Neurospora crassa*, etc.

The enzyme amount present in the final composition may widely vary but is generally from $5.10^{-3}$ to 5 mg, preferably from $5.10^{-2}$ to 0.5 mg par mL of the final composition.

Further, the dyeing compositions may more particularly contain at least one surfactant in the proportion of at least 0.01% by weight, and preferably a surfactant with a non ionic nature.

The surfactants may be selected from anionic, cationic, non ionic, amphoteric agents or the mixtures thereof, and preferably amongst non ionic surfactants.

Such surfactants include alkylbenzenesulfonates, alkyl-naphthalene-sulfonates, sulfates, sulfate ethers and fatty alcohol sulfonates, quaternary ammonium salts, such as trimethylcetylammonium bromide, cetylpyridinium bromide; optionally oxyethylated fatty acid ethanolamides; polyoxyethylated acids, alcools or amines, polyglycerolated alcools, polyoxyethylated or polyglycerolated alkylphenols, as well as polyoxyethylated alkylsulfates.

The surfactant amounts present in the compositions according to the invention may vary from 0.01 to 40% and preferably from 0.5 to 30% based on the total weight of the composition.

The thickening agents that can be added to the compositions according to the invention may be selected amongst sodium alginate, Arabic gum, cellulose derivates, acrylic acid polymers, xanthane gum. Mineral thickening agents such as bentonite may also be used.

Such thickening agents are preferably present in proportions ranging from 0.1 to 5% and in particular from 0.2 to 3% by weight based on the total weight of the composition.

Such compositions can also contain other cosmetically acceptable builders, such as, for example penetration agents, perfumes, buffers, etc.

The compositions according to the invention can also comprise any conventional builder, in usual proportion, which is not detrimental to the desired properties, particularly the coloring effect of the compositions.

The coloring composition can also contain an effective amount of other agents, further previously known in oxidation coloration, such as various usual builders like UV filters, waxes, volatile or non volatile cyclic or linear or branched, organomodified (more particularly by amine groups) or not silicones, preservatives, ceramides, pseudoceramides, vegetable, mineral or synthesis oils, vitamins or provitamins such as panthenol, opacifiers, etc.

Such organic UV filters may be more particularly selected amongst cinnamic derivates; dibenzoylmethane derivates; salicylic derivates, camphor derivates; triazine derivates such as those disclosed in patent applications U.S. Pat. No. 4,367,390, EP-0.863.145, EP-0.517.104, EP-0.570.838, EP-0.796.851, EP-0.775.698, EP-0.878.469, EP-0.933.376 and EP-0.893.119; benzophenone derivate; β-β'-diphenylacrylate derivates, benzimidazole derivates; bis-benzoazolyl derivates such as those disclosed in Patents EP-0,669,323 and U.S. Pat. No. 2,463,264; methylene-bis-(hydroxyphenylbenzotriazole) derivates such as those disclosed in patent applications U.S Pat. No. 5,237,071, U.S. Pat. No. 5,166,355, GB-230549, DE-19726184 and EP-0.893.119; p-aminobenzoic acid derivates; dimers derived from α-alkylstyrene as disclosed in Patent Application DE-198556-49; hydrocarbon filter polymers and filter silicones such as those disclosed, for example, in Patent Application WO 93/04665. Pigments or nanopigments (average size of the primary particles: generally between 5 nm and 10 nm, preferably between 10 nm and 50 nm) of metallic oxides, coated or not, such as for example, nanopigments of titania (amorphous or cristallized in a rutile and/or anatase form), iron, zinc, zirconium or cerium, which are all well known UV photoprotective agents, can also be used. Conventional coating agents are further alumina and/or aluminium stearate. Such nanopigments of metallic oxides, coated or not coated, are disclosed in particular in Patent Applications EP-0.518.772 and EP-0.518.773.

Obviously, the man of the art will take care to select the above mentioned complementary optional compound(s) so that the advantageous properties intrinsically associated to the dyeing composition according to the invention are not or not substantially altered by the contemplated addition(s).

The oxidation dye amount, in particular orthodiphenol, in the final composition should be sufficient to obtain a visible coloring. Such an amount may vary in broad ranges depending on the nature of the oxidation dye and of the desired intensity of the coloration.

Generally speaking, a suitable coloration will be obtained when the dye amount is such that the orthodiphenol oxidation dye content in the final coloring composition is at least 0.1 micromole, preferably at least 1 micromole par mL of the final composition.

Typically, the orthodiphenol oxidation dye amount in the final composition ranges from 1 mM to 10 mM per liter and generally, in the order of 5 mM per liter.

Varying the nature of the various oxidation dyes and the proportions thereof in the composition, the color of the final coloring composition may be varied. A color range is thereby obtained.

For example, with a 1/10 ratio of chlorogenic acid/catechin, a light brown color is obtained and with a 1/1 ratio a mahogany color.

The physiologically acceptable medium is a solid or liquid medium which is neither detrimental to the coloring property of the oxidation dyes nor to the reducing effect of the absorption and the transcutaneous passage of the system.

The physiologically acceptable medium is preferably a solubilizing medium for the oxidation dye and having a bacteriostatic property.

Dye solvents suitable for formulating compositions according to the invention include water, alcohols, solvents and the mixtures thereof.

The alcohols are preferably ($C_1$–$C_6$) lower alkanols such as ethanol and isopropanol and alkanediols such as ethylene glycol, propylene glycol and pentane diol.

Solvents include ethers, esters (particularly acetates), dimethylsulfoxide (DMSO), N-methylpyrrolidone (NMP), ketones (particularly acetone) and the mixtures thereof.

The physiologically acceptable medium preferably comprises water (in particular distilled or permuted) or a water/alcohol mixture, particularly water/ethanol.

The amount of alcohol in the water/alcohol mixture may account for 80% by weight of the water/alcohol mixture, preferably from 1 to 50% by weight and preferably from 5 to 20% by weight.

The physiologically acceptable medium may be a solid medium such as an excipient for formulating shingles and tablets, in particular effervescent ones.

Preferably, the compositions according to the invention are free from chelatants of the Mn(II) and/or Zn(II) salts being used, as such agents tend to inhibit the dye oxidation.

In order to reveal the composition coloration according to the invention, it is sufficient to put the composition containing at least one oxidation dye and an efficient amount of the system according to the invention in the presence of a oxidizing medium such as an oxygen-containing medium (for example, oxygen from the air).

The compositions according to the invention are useful for coloring keratin fibres such as hair, eye-lashes, eyebrows and hairs.

For coloring keratin fibres, various methods for coating compositions according to the invention can be used.

According to a first method, a composition is coated on the keratin fibres, in the presence of oxygen, for example, oxygen from the air, which composition comprises all the ingredients of the composition, i.e. both the oxidation dye(s) and the system limiting the transcutaneous passage.

According to a second method, one can first coat on the keratin fibres and/or on the hair, a film of the system limiting the transcutaneous passage in a physiologically acceptable medium, followed by the application, on the keratin fibres, of a film of a basic composition of one or more oxidation dyes in a physiologically acceptable medium which, in the presence of oxygen, will reveal the coloring of the basic composition.

One can revert, but this is not advisable, the coating order of the films.

Coating the films can be performed using any know means, more particularly, through spraying.

The compositions according to the invention may be present and packed under various forms, such as creams, masks, sprays, lotions, etc.

In particular, the composition is in the form of two separate components, a first component comprising the system dissolved in a physiologically acceptable medium, and a second component comprising the oxidation dye dissolved in a physiologically acceptable medium.

According to a first embodiment, the compositions according to the invention may be packed in the form of an one container spray where the dye-containing composition and the system reducing the absorption and the transcutaneous passage of the dyes and a conventional inert propellant such as nitrogen, a saturated hydrocarbon such as isopropane or a fluorinated hydrocarbon, for example, a Freon®, are located.

In a second embodiment, the composition according to the invention may be packed in the form of a kit comprising two distinct containers, one for the basic composition containing the dye(s) and the other for the system, the basic composition and the system being blended or successively coated at the time of use.

In a third embodiment, the composition can be contained in an one container pump system, with no air intake, or in a two container pump system, the basic composition being in one container and the system reducing the absorption and the transcutaneous passage in the other.

In a fourth embodiment, the composition according to the invention may have the form of shingles. Each shingle may comprise, being blended with an excipient, the dye(s) and the system, the excipient preventing the reaction in the presence of oxygen and the dye(s) and the system being contained in distinct shingles.

When cleaving either the single shingle or one shingle of each component, for example, in water, the coloring composition according to the invention is provided.

The shingles, as it is conventional, may be effervescent shingles.

The excipient being used may be any conventional excipient such as a mixture of talc, stearate (in particular magnesium stearate), citric acid and/or tartaric acid, alkaline and/or alkaline earth hydrogenocarbonate.

The citric acid and/or tartaric acid amount being present should be such that there is no neutralization of the hydrogenocarbonate resulting in a lack of free hydrogenocarbonate relative to Mn(II) and/or Zn(II).

Thus, the shingle comprises an excipient containing citric acid and/or tartaric acid in a substoïchiometric amount relative to the alkaline and/or alkaline earth hydrogenocarbonate.

On the other hand, since water, more particularly tap water and some spring or mineral waters, generally contains manganese (II), it is sometimes satisfactory to put in the water the only shingle containing hydrogenocarbonate and the oxidation dye(s), the Mn(II) content of the system reducing the absorption and the transcutaneous passage being then provided by the Mn(II) present in water.

Similarly, some vegetable extracts (for example, tea leaf extracts) may contain large amounts of manganese (II). Depending on such contents, an adjustment of the concentrations of the system is performed so as to have a satisfactory result.

Obviously, the coloration intensity may be varied by cleaving several shingles in water.

On the other hand, the coloring rate may be accelerated adding to the composition an oxygen-generating compound or compound formulation, for example through contact with water. Thus, such a compound or formulation, for example sodium peroxide, may be incorporated into the shingle.

The remainder of the disclosure refers to the single figure which is a diagram of the penetration rate of a coloring composition according to the invention having an analogous composition which does not comprise a system for limiting the transcutaneous passage of the oxidation dye.

EXAMPLES

Having generally described this invention, a further understanding can be obtained by reference to certain specific examples which are provided herein for purposes of illustration only and are not intended to be limiting unless otherwise specified.

i) Experimentation

The 5,6-dihydroxyindole mixture with the system limiting the transcutaneous passage has been prepared fresh by adding an system equivalent volume (=1 mM MnCl$_2$ in 1 M NaHCO$_3$; pH=10) to an aqueous solution of 10 mM 5,6-dihydroxyindole. Then, it has been coated on rebuilt skin (for example Epiderm® from Mattek, Inc., Episkin® from Episkin SNC or Skinethic® from Skinethic Laboratories) placed in diffusion cells in a static diffusion mode at a dose of 250 mg·cm$^2$ for 16 hours. The analysis of the penetration rates of 5,6-dihydroxyindole through the skin has been conducted through VIS spectrophotometry through the oxidation products thereof. The 5,6-dihydroxyindole range has been prepared as follows. A plurality of dilutions from 0 to 0.5 mM 5,6-dihydroxindole in receiving liquid has been left for 16 hours at 32° C. for forming oxidation products in the form of a pigment. Such pigments absorb visible light (VIS) ("scattering" effect) depending on their concentration, which is directly related to the initial 5,6-dihydroxyindole concentration. Thus, the 5,6-dihydroxyindol range has been obtained through VIS absorption of such pigments formed after 5,6-dihydroxyindole oxydation. A 1:1 mixture between 10 mM 5,6-dihydroxyindole and distilled water has been used as a control.

ii) Results

The results of the mixtures containing 5,6-dihydroxyindole at a final concentration of 5 mM are shown in FIG. 1. At 5 mM of 5,6-dihydroxyindole of final concentration, the penetration rate of the 5,6-dihydroxyindole is approximately 3% of the dose coated with no system (=control mixture) and lower than 0.5% with the system after a 16 hour coating at an infinite dose. The 5,6-dihydroxyindole penetration through the skin has therefore been significantly decreased by the presence of the system.

The following embodiments 1–55 are preferred.

1. The use, in a composition for coloring the keratin fibres comprising, in a physiologically acceptable medium, an effective amount of at least one orthodiphenol oxidation dye, as an agent for limiting the transcutaneous passage of the oxidation dye, of an effective amount of a system comprising a first component selected amongst Mn(II) and/or Zn(II) salts and oxides and a second component selected amongst alkaline hydrogenocarbonates, alkaline earth hydrogenocarbonates and the mixtures thereof, the proportions of the first component and the second component being such that:

$$\frac{[Mn(II)]}{[HCO_3]} \leq 1 \text{ avec } [Mn(II)] \neq 0$$

$$\frac{[Zn(II)]}{[HCO_3]} \leq 1 \text{ avec } [Zn(II)] \neq 0$$

$$\frac{[Mn(II) + Zn(II)]}{[HCO_3]} \leq 1 \text{ avec } [Mn(II)] \text{ et } [Zn(II)] \neq 0$$

where [Mn(II)], [Zn(II)] and [HCO$_3$] respectively represent the molar concentrations of Mn(II), Zn(II) and HCO$_3$ in the composition, the limitation of the transcutaneous passage of the oxidation dye leading to a better dye tolerance and the prevention of skin staining.

2. A use according to preferred embodiment 1, characterized in that the $$\left[\frac{Mn(II)}{HCO_3}\right]$$

ratio ranges from $10^{-5}$ to $10^{-1}$.

3. A use according to preferred embodiment 1 or 2, characterized in that the

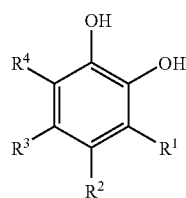

ratio ranges from $10^{-4}$ to <1.

4. A use according to any one of preceding preferred embodiments, characterized in that $$\frac{[Mn(II) + Zn(II)]}{[HCO_3]}$$

ratio ranges from $10^{-5}$ to $10^{-1}$.

5. A use according to any one of preceding preferred embodiments, characterized in that the Mn(II) and Zn(II) salts are selected amongst chloride, fluoride, iodide, sulfate, phosphate, nitrate, perchlorate, carboxylic acid salts and the mixtures thereof.

6. A use according to preferred embodiment 5, characterized in that the Mn(II) and/or Zn(II) salt is chloride.

7. A use according to preferred embodiment 5, characterized in that the carboxylic acid salts are hydroxylated carboxylic acid salts.

8. A use according to preferred embodiment 7, characterized in that the hydroxylated carboxylic acid salt is gluconate.

9. A use according to any one of preceding preferred embodiments, characterized in that the hydrogenocarbonate is selected amongst sodium hydrogenocarbonate, potassium hydrogenocarbonate and the mixtures thereof.

10. A use according to any one of preceding preferred embodiments, characterized in that the orthodiphenol dye comprises a benzene ring or a condensed aromatic ring carrying at least two hydroxyl groups on two consecutive carbon atoms of the ring.

11. A use according to preferred embodiment 10, characterized in that the orthodiphenol is a compound of formula:

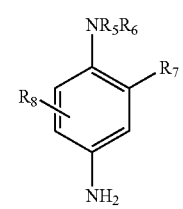

(I)

where the $R^1$ to $R^4$ substituents are identical or different and represent a hydrogen atom, a halogen, hydroxyl, carboxyl, alkyl carboxylate, optionally substituted amino, linear or branched optionally substituted alkyl, linear or branched optionally substituted alkenyl, optionally substituted cycloalkyl, alkoxy, alkoxyalkyl, alkoxyaryl, the aryl group optionally being substituted, aryl, substituted aryl and optionally substituted heterocyclic moiety, a moiety containing one or more silicon atoms, wherein two of the $R^1$ to $R^4$ substituants form together a saturated or unsaturated ring optionally containing one or more heteroatoms or optionally condensed with one or more saturated or unsaturated rings optionally containing one or more heteroatoms.

12. A use according to preferred embodiment 10, characterized in that the oxidation dye is selected amongst flavanols, flavonols, anthocyaninidins, anthocyanins, hydroxybenzoates, flavones, iridoids, such compounds being optionally able to be osylated and/or in the form of oligomers, optionally osylated hydroxystilbenes, 3,4-dihydroxyphenylalanine and the derivates thereof, 2,3-dihydroxyphenylalanine and the derivates thereof, 4,5-dihydroxyphenylalanine and the derivates thereof, 4,5-dihydroxyindole and the derivates thereof, 6,7-dihydroxyindole and the derivates thereof, 2,3-dihydroxyindole and the derivates thereof, dihydroxycinnamates, hydroxycoumarins, hydroxyisocoumarins, hydroxycoumarones, hydroxyisocoumarones, hydroxychalcones, hydroxychromones, anthocyans, quinones, hydroxyxanthones, and the mixtures of two or more of the above-mentioned compounds.

13. A use according to preferred embodiment 12, characterized in that the oxidation dye is 5,6-dihydroxyindole or 5,6-dihydroxyindolecarboxylic acid.

14. A use according to any one of preferred embodiments 10 to 13, characterized in that the orthodiphenol dye is contained in plant, fruit, citrus, vegetable extracts or the mixtures thereof.

15. A use according to preferred embodiment 14, characterized in that the orthodiphenol oxidation dye is contained in tea, grape, apple, banana, potato extracts or the mixtures thereof.

16. A use according to any one of preceding preferred embodiments, characterized in that the composition for coloring keratin fibres additionally comprises a second oxidation dye selected amongst oxidation bases, coupling agents and mixtures thereof.

17. A use according to preferred embodiment 16, characterized in that the oxidation bases are selected amongst ortho- and para-phenylenediamines, double bases, ortho and para-aminophenols, heterocyclic bases as well as addition salts of all such compounds with an acid.

18. A use according to preferred embodiment 17, characterized in that the oxidation base is selected amongst para-phenylenediamines of the following formula:

(II)

where:
$R_5$ represents a hydrogen atom, $C_1$–$C_4$ alkyl, $C_1$–$C_4$ monohydroxyalkyl, $C_2$–$C_4$ polyhydroxyalkyl, $(C_1$–$C_4)$alkoxy $(C_1$–$C_4)$alkyle, nitrogen-substituted $C_1$–$C_4$ alkyl, phenyl or 4'-aminophenyl moieties;

$R_6$ represents a hydrogen atom, $C_1$–$C_4$ alkyl, $C_1$–$C_4$ monohydroxyalkyl or $C_2$–$C_4$ polyhydroxyalkyl, $(C_1$–$C_4)$alkoxy $(C_1$–$C_4)$alkyl or nitrogen-substituted $C_1$–$C_4$ alkyl moieties;

$R_7$ represents a hydrogen atom, a halogen atom, such as a chlorine atom, $C_1$–$C_4$ alkyl, sulfo, carboxy, $C_1$–$C_4$ monohydroxyalkyl or $C_1$–$C_4$ hydroxyalkoxy, $C_1$–$C_4$ acetylaminoalkoxy, $C_1$–$C_4$ mesylaminoalkoxy or $C_1$–$C_4$ carbomoylaminoalkoxy moieties;

$R_8$ represents a hydrogen, a halogen atom or a $C_1$–$C_4$ alkyl moiety;

$R_5$ and $R_6$ may also form together with the nitrogen atom carrying them a 5 or 6 ring member nitrogen heterocycle optionally substituted by one or more alkyl, hydroxy or ureido groups.

19. A use according to preferred embodiment 18, characterized in that the paraphenylenediamines are selected amongst paraphenylenediamine, paratoluylenediamine, 2-chloro-paraphenylenediamine, 2-isopropyl-paraphenylenediamine, 2-β-hydroxyethylparaphenylenediamine, 2-β-hydroxyethyloxy-paraphenylenediamine, 2,6-dimethyl-paraphenylene-diamine, 2,6-diethyl-paraphenylenediamine, 2,3-dimethyl-paraphenylene-diamine, N,N-bis-(β-hydroxyethyl)-paraphenylenediamine, 2-chloro-para-phenylenediamine and the addition salts thereof with an acid.

20. A use according to preferred embodiment 17, characterized in that the double bases are selected amongst the compounds of the formula (III):

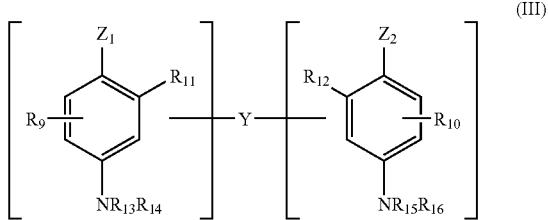

(III)

where:

$Z_1$ and $Z_2$ are identical or different and represent a hydroxyl or —$NH_2$ moiety which may be substituted by a $C_1$–$C_4$ alkyl moiety or by a linking arm Y;

the linking arm Y represents a linear or branched alkylene chain comprising from 1 to 14 carbon atoms, which may be interrupted or terminated by one or more nitrogen groups and/or by one or more heteroatoms such as oxygen, sulfur or nitrogen atoms and optionally substituted by one or more $C_1$–$C_6$ hydroxyl or alkoxy moieties;

$R_9$ and $R_{10}$ represent a hydrogen or halogen atom, $C_1$–$C_4$ alkyl, $C_1$–$C_4$ monohydroxyalkyl, $C_2$–$C_4$ polyhydroxyalkyl, $C_1$–$C_4$ aminoalkyl moieties or a linking arm Y;

$R^{11}$, $R_{12}$, $R_{13}$, $R_{14}$, $R_{15}$ and $R_{16}$ are identical or different and represent a hydrogen atom, a linking arm Y or a $C_1$–$C_4$ alkyl moiety, provided that the compounds of the formula (III) only comprise one linking arm Y per molecule.

21. A use according to preferred embodiment 20, characterized in that the double bases are selected amongst N,N'-bis-(β-hydroxyethyl)-N,N'-bis-(4'-aminophenyl)-1,3-diamino propanol, N,N'-bis-(β-hydroxyethyl)-N,N'-bis-(4'-aminophenyl)ethylenediamine, N,N'-bis-(4-aminophenyl) tetra-methylenediamine, N,N'-bis-(β-hydroxyethyl)-N,N'-bis-(4-aminophenyl)tetramethylenediamine, N,N'-bis-(4-methyl-aminophenyl) tetramethylene-diamine, N,N'-bis-(ethyl)-N,N'-bis-(4'-amino,3'-methylphenyl)ethylenediamine, 1,8-bis-(2,5-diaminophenoxy)-3,5-dioxaoctane and the addition salts thereof with an acid.

22. A use according to preferred embodiment 17, characterized in that the oxidation base is selected amongst para-aminophenols of the formula (IV):

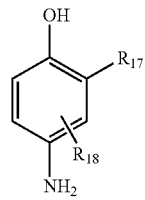

(IV)

where:

$R_{17}$ represents a hydrogen atom, a halogen atom such as fluorine or chlorine, $C_1$–$C_4$ alkyl, $C_1$–$C_4$ monohydroxyalkyl, ($C_1$–$C_4$)alkoxy($C_1$–$C_4$)alkyl or $C_1$–$C_4$ aminoalkyl or ($C_1$–$C_4$)hydroxyalkyl($C_1$–$C_4$)aminoalkyl moieties; and $R_{18}$ represents a hydrogen atom or a halogen atom such as fluorine or chlorine, $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alcoxy($C_1$–$C_4$)alkyl moieties.

23. A use according to preferred embodiment 22, characterized in that the para-aminophenols are selected amongst para-aminophenol, 4-amino-3-methyl-phenol, 4-amino-3-fluoro-phenol, 4-amino-3-hydroxymethyl-phenol, 4-amino-2-methyl-phenol, 4-amino-2-hydroxymethyl-phenol, 4-amino-2-methoxymethyl-phenol, 4-amino-2-aminomethyl-phenol, 4-amino-2-(β-hydroxyethyl-aminomethyl)-phenol and the addition salts thereof with an acid.

24. A use according to preferred embodiment 17, characterized in that the oxidation base is an orthoaminophenol selected amongst 2-amino-phenol, 2-amino-1-hydroxy-5-methyl-benzene, 2-amino-1-hydroxy-6-methyl-benzene, 5-acetamido-2-amino-phenol and the addition salts thereof with an acid.

25. A use according to preferred embodiment 17, characterized in that the oxidation base is a heterocyclic base selected amongst the pyridin derivates, the pyrimidin derivates, the pyrazol derivates and the addition salts thereof with an acid.

26. A use according to preferred embodiment 25, characterized in that the pyridine derivates are selected amongst 2,5-diamino-pyridine, 2-(4-methoxyphenyl)amino-3-amino-pyridine, 2,3-diamino-6-methoxy-pyridine, 2-(β-methoxyethyl)amino-3-amino-6-methoxypyridine and 3,4-diamino-pyridine.

27. A use according to preferred embodiment 25, characterized in that the pyrimidine derivates are selected amongst 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and pyrazolo-pyrimidine derivates such as those mentioned in Patent Application FR-A-2,750,048 and amongst which one can mention pyrazolo-[1,5-a]-pyrimidine-3,7-diamine, 2,5-dimethyl-pyrazolo-[1,5]-pyrimidine-3,7-diamine; 2,5-dimethyl-pyrazolo-[1,5-a]-pyrimidine-3,7-diamine, pyrazolo-[1,5-a]-pyrimidine-3,5-diamine, 2,7-dimethyl-pyrazolo-[1,5-a]-pyrimidine-3,5-diamine, 3-amino-pyrazolo-[1,5-a]-pyrimidin-7-ol, 3-amino-pyrazolo-[1,5-a]-pyrimidin-5-ol, 2-(3-amino-pyrazolo-[1,5-a]-pyrimidin-7-ylamino)-ethanol, 2-(7-amino-pyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo[1,5-a]pyrimidin-3-yl)-(2-hydroxy-ethyl)-amino]-ethanol, 5,6-dimethyl-pyrazolo-[1,5-a]-pyrimidine-3,7-diamine, 2,6-dimethyl-pyrazolo-[1,5-a]-pyrimidine-3,7- diamine, 2,5, N7,N7-tetramethyl-pyrazolo-1 [1,5-a]-pyrimidine-3,7-diamine, 3-amino-5-methyl-7-imidazolylpropylamino-pyrazolo-[1,5-a]-pyrimidine and the addition salts and tautomeric forms thereof, when there is a tautomeric equilibrium.

28. A use according to preferred embodiment 25, characterized in that the pyrazolic derivates are selected amongst 4,5-diamino-1-methyl-pyrazole, 3,4-diamino-pyrazole, 4,5-diamino-1-(4'chlorobenzyl)-pyrazole, 4,5-diamino 1,3-dimethyl-pyrazole, 4,5-diamino-3-methyl-1-phenyl-pyrazole, 4,5-diamino-1-methyl-3-phenyl-pyrazole, 4-amino-1,3-dimethyl-5-hydrazino-pyrazole, 1-benzyl-4,5-diamino-3-methyl-pyrazole, 4,5-diamino-3-tert-butyl-1-methyl-pyrazole, 4,5-diamino-1-tert-butyl-3-methyl-pyrazole, 4,5-diamino-1-(β-hydroxyethyl)-3-methyl-pyrazole, 4,5-diamino-1-(β-hydroxy-ethyl)-pyrazole, 4,5-diamino-1-ethyl-3-methyl-pyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methyl-pyrazole, 4,5-diamino-3-hydroxymethyl-1-isopropyl-pyrazole, 4,5-diamino-3-methyl-1-isopropyl-pyrazole, 4-amino-5-(2 '-aminoethyl)amino-1,3-dimethyl-pyrazole, 3,4,5-triamino-pyrazole, 1-methyl-3,4,5-triamino-pyrazole, 3,5-diamino-1-methyl-4-methylamino-pyrazole and 3,5-diamino-4-(β-hydroxy-ethyl)amino-1-methyl-pyrazole.

29. A use according to any one of preceding preferred embodiments, characterized in that the oxidation base accounts for 0.0005 to 12% by weight based on the total weight of the composition and preferably, 0.005 to 8%.

30. A use according to preferred embodiment 16, characterized in that the coupling agents are selected amongst meta-aminophenol, meta-phenylenediamines, metadiphenols, the naphthols and heterocyclic coupling agents such as, for example indolic derivates, indolinic derivates, sesamol and the derivates thereof, pyridinic derivates, pyrazolotriazole derivates, pyrazolones, indazoles, benzimidazoles, benzothiazoles, benzoxazoles, 1,3-benzodioxoles, quinolines and the addition salts thereof with an acid.

31. A use according to preferred embodiment 30, characterized in that the coupling agents are selected amongst 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethyl amino)-1-methoxybenzene, 1,3-diaminobenzene, 1,3-bis-(2,4-diaminophenoxy) propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindolin, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo-[3,2-c]-1,2,4-triazole, 2,6-dimethyl-pyrazolo-[1,5-b]-1,2,4-triazole and the addition salts thereof with an acid.

32. A use according to preferred embodiment 30 or 31, characterized in that the coupling agent(s) account(s) for 0.0001 to 15% by weight of the total weight of the composition and preferably, 0.001 to 10%.

33. A use according to any one of preceding preferred embodiments, characterized in that it comprises one or more amino acids and/or one or more proteins.

34. A use according to preferred embodiment 38, characterized in that the amino acid(s) comprise(s) at least one thiol group and are selected amongst those amino acids having an amine function in an α-position relative to a carboxylic acid function.

35. A use according to preferred embodiment 34, characterized in that the amino acid(s) is(are) selected amongst cysteine and the derivates thereof, proteins are selected from glutathione and the derivates thereof.

36. A use according to any one of preferred embodiments 33 to 35, characterized in that the molar ratio of the amino acid(s) and of the protein(s) to the oxidation dye(s) ranges from 0.001 to 50, preferably from 0.01 to 5 and more preferably from 0.05 to 2.5.

37. A use according to any one of preceding preferred embodiments, characterized in that the composition additionally comprises an enzyme.

38. A use according to preferred embodiment 37, characterized in that the enzyme is selected amongst pyranose oxidases, glucose oxidases, glycerol oxidases, lactate oxidases, pyruvate oxidases, uricases, choline oxidases, sarcosine oxidases, bilirubin oxidases, laccases, tyrosinases, peroxydases, catalases, superoxid dimutases and the mixtures thereof, or amongst vegetable or animal extracts containing the above-mentioned enzymes.

39. A use according to preferred embodiment 38, characterized in that the enzyme is selected amongst tyrosinases.

40. A use according to preferred embodiment 37 to 39, characterized in that it comprises from $5.10^{-3}$ to 5 mg, preferably from $5.10^{-2}$ to 0.5 mg enzyme per mL of the final composition.

41. A use according to any one of preceding preferred embodiments, characterized in that the orthodiphenol oxidation dye is present in an amount of 1 mM to 10 mM per liter of composition.

42. A use according to any one of preceding preferred embodiments, characterized in that the physiologically acceptable medium is a solubilizing medium for the oxidation dye, preferably with a bacteriological property.

43. A use according to any one of preceding preferred embodiments, characterized in that the physiologically acceptable medium comprises a solvent or a mixture of solvents of the dye.

44. A use according to preferred embodiment 43, characterized in that the solvent is selected amongst water, alcohols, ethers, dimethylsulfoxide, N-methylpyrrolidone, acetone and the mixtures thereof.

45. A use according to preferred embodiment 44, characterized in that the alcohol is an alkanol or an alkanediol.

46. A use according to preferred embodiment 44, characterized in that the solvent is a water/alcohol mixture.

47. A use according to preferred embodiment 46, characterized in that the alcohol accounts for up to 80% by weight of the mixture, preferably 1 to 50% by weight and preferably 5 to 20% by weight.

48. A use according to any one of preceding preferred embodiments, characterized in that the composition is free from any chelatant of the Mn(II) and/or Zn(II) salts.

49. A use according to any one of preceding preferred embodiments, characterized in that the composition is in the form of two separate components, a first component comprising the system dissolved in a physiologically acceptable medium and a second component comprising the oxidation dye dissolved in a physiologically acceptable medium.

50. A use according to any one of preferred embodiments 1 to 48, characterized in that the composition is packed in the form of a spray or a pump system with no air intake.

51. A use according to preferred embodiment 50, characterized in that the composition is packed in a pump system with two distinct containers, each of the components being separately contained in one of both containers.

52. A use according to any of preferred embodiments 1 to 48, characterized in that the composition is packed in the form of a shingle.

53. A use according to preferred embodiment 52, characterized in that the shingle comprises an excipient containing citric acid and/or tartaric acid in a substoïchiometric amount relative to the alkaline and/or alkaline earth hydrogenocarbonate.

54. A use according to any one of preferred embodiments 1 to 48, characterized in that the composition is packed in the form of two shingles, one shingle comprising the system and an excipient and a second shingle comprising the dye and an excipient.

55. A use according to any one of preferred embodiments 52 to 54, characterized in that the shingle(s) is(are) effervescent shingle(s).

The entire contents of each of the above-identified references, patents, applications and published applications are hereby incorporated by reference, the same as if set forth at length.

Having now fully described this invention, it will be apparent to one of ordinary skill in the art that many changes and modifications can be made thereto without departing from the spirit or scope of the invention as set forth herein.

The invention claimed is:

1. A method of reducing transcutaneous passage of an oxidation dye of a composition, comprising:
    a physiologically acceptable medium,
    at least one orthodiphenol oxidation dye, and
    at least one second oxidation dye,
    wherein the method comprises adding to the composition, a catalytic system comprising at least one first component selected from the group consisting of Mn(II) salt, Mn(II) oxide, Zn(II) salt, Zn(II) oxide, and combinations thereof,
    and at least one second component selected from the group consisting of alkaline hydrogencarbonate, alkaline earth hydrogencarbonate, and mixtures thereof,
    wherein at least one of the following equations are satisfied:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

where $[Mn(II)]$, $[Zn(II)]$ and $[HCO_3]$ respectively represent the molar concentrations of $Mn(II)$, $Zn(II)$ and $HCO_3$ in the composition, wherein the second oxidation dye is one or more of:
(i) an oxidation base selected from the group consisting of ortho- and para-phenylenediamine, double base, ortho-aminophenol, para-aminophenol, heterocyclic base, acid addition salt thereof, and mixtures thereof;
(ii) a para-phenylenediamine of the following formula:

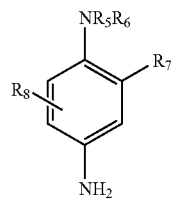

(II)

where:
    $R_5$ represents a hydrogen atom, $C_1$–$C_4$ alkyl, $C_1$–$C_4$ monohydroxyalkyl, $C_2$–$C_4$ polyhydroxyalkyl, $(C_1$–$C_4)$ alkoxy$(C_1$–$C_4)$ alkyle, nitrogen-substituted $C_1$–$C_4$ alkyl, phenyl or 4'-aminophenyl moieties;
    $R_6$ represents a hydrogen atom, $C_1$–$C_4$ alkyl, $C_1$–$C_4$ mono-hydroxyalkyl or $C_2$–$C_4$ polyhydroxyalkyl, $(C_1$–$C_4)$alkoxy$(C_1$–$C_4)$ alkyl or nitrogen-substituted $C_1$–$C_4$ alkyl moieties;
    $R_7$ represents a hydrogen atom, a halogen atom, such as a chlorine atom, $C_1$–$C_4$ alkyl, sulfo, carboxy, $C_1$–$C_4$ monohydroxyalkyl or $C_1$–$C_4$ hydroxyalkoxy, $C_1$–$C_4$ acetylaminoalkoxy, $C_1$–$C_4$ mesylaminoalkoxy or $C_1$–$C_4$ carbomoylaminoalkoxy moieties;
    $R_8$ represents a hydrogen, a halogen atom or a $C_1$–$C_4$ alkyl moiety; $R_5$ and $R_6$ may also form together with the nitrogen atom carrying them a 5 or 6 ring member nitrogen heterocycle optionally substituted by one or more alkyl, hydroxy or ureido groups;
(iii) a double base selected from the group consisting of double bases having the formula (III):

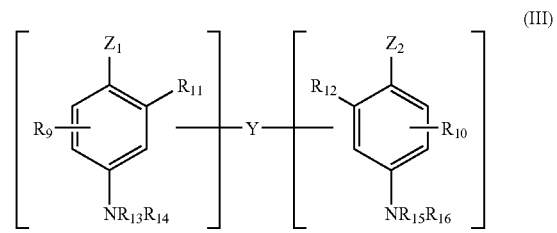

where:
    $Z_1$ and $Z_2$ are identical or different and represent a hydroxyl or $—NH_2$ moiety which may be substituted by a $C_1$–$C_4$ alkyl moiety or by a linking arm Y;
    the linking arm Y represents a linear or branched alkylene chain comprising from 1 to 14 carbon atoms, which may be interrupted or terminated by one or more nitrogen groups and/or by one or more heteroatoms such as oxygen, sulfur or nitrogen atoms and optionally substituted by one or more $C_1$–$C_6$ hydroxyl or alkoxy moieties;
    $R_9$ and $R_{10}$ represent a hydrogen or halogen atom, $C_1$–$C_4$ alkyl, $C_1$–$C_4$ monohydroxyalkyl, $C_2$–$C_4$ polyhydroxyalkyl, $C_1$–$C_4$ aminoalkyl moieties or a linking arm Y;
    $R_{11}$, $R_{12}$, $R_{13}$, $R_{14}$, $R_{15}$, and $R_{16}$ are identical or different and represent a hydrogen atom, a linking arm Y or a $C_1$–$C_4$ alkyl moiety,
provided that the compounds of the formula (III) only comprise one linking arm Y per molecule
(iv) an oxidation base is selected from the group consisting of one or more para-aminophenols of the formula (IV):

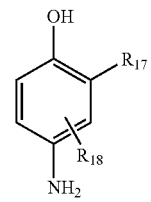

(IV)

where:
    $R_{17}$ represents a hydrogen atom, a halogen atom such as fluorine or chlorine, $C_1$–$C_4$ alkyl, $C_1$–$R_4$ monohydroxyalkyl, $(C_1-R_4)$alkoxy$(C_1-C_4$alkyl or $C_1-C_4$ aminoalkyl or $(C_1-R_4)$hydroxyalkyl$(C_1-C_4)$aminoalkyl group; and $R_{18}$ represents a hydrogen atom or a halogen atom such as fluorine or chlorine, $C_1-C_4$ alkyl, $C_1-C_4$ monohydroxyalkyl, $C_1-C_4$ polyhydroxyalkyl, $C_1-C_4$ aminoalkyl, $C_1-C_4$ cyanoalkyl or $(C_1-C_4)$alcoxy$(C_1-C_4)$alkyl group;

(v) an orthoaminophenol selected from the group consisting of 2-amino-phenol, 2-amino-1-hydroxy-5-methylbenzene, 2-amino-1-hydroxy-6-methyl-benzene, 5-acetamido-2-amino-phenol, acid addition salt thereof, and mixtures thereof;

(vi) a heterocyclic base selected from the group consisting of pyridine derivate, pyrimidine derivate, pyrazole derivate, acid addition salt thereof, and mixtures thereof; and (vii) a coupling agent selected from the group consisting of meta-aminophenol, meta-phenylenediamine, metadiphenol, naphthol, heterocyclic coupling agent, indolic derivate, indolinic derivate, sesamol, sesamol derivate, pyridinic derivate, pyrazolotriazole derivate, pyrazolone, indazole, benzimidazole, benzothiazole, benzoxazole, 1,3-benzodioxole, quinoline, 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis-(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindolin, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo-[3,2-c]-1,2,4-triazole, 2,6-dimethyl-pyrazolo-[1,5-b]-1,2,4-triazole, acid addition salt thereof, and mixtures thereof.

2. The method according to claim 1, wherein the $$\left[\frac{Mn(II)}{HCO_3}\right]$$

ratio ranges from $10^{-5}$ to $10^{-1}$.

3. The method according to claim 1, wherein the $$\left[\frac{Zn(II)}{HCO_3}\right]$$

ratio ranges from $10^{-4}$ to $<1$.

4. The method according to claim 1, wherein the $$\frac{[Mn(II)+Zn(II)]}{[HCO_3]}$$

ratio ranges from $10^{-5}$ to $10^{-1}$.

5. The method according to claim 1, wherein the Mn(II) and Zn(II) salts are selected from the group consisting of chloride, fluoride, iodide, sulfate, phosphate, nitrate, perchlorate, carboxylic acid salts and mixtures thereof.

6. The method according to claim 1, wherein the Mn(II) and/or Zn(II) salt is a chloride salt.

7. The method according to claim 1, wherein the Mn(II) and/or Zn(II) salt is a hydroxylated carboxylic acid salt.

8. The method according to claim 1, wherein the Mn(II) and/or Zn(II) salt is a gluconate salt.

9. The method according to claim 1, wherein the hydrogencarbonate is selected from the group consisting of sodium hydrogencarbonate, potassium hydrogencarbonate, and mixtures thereof.

10. The method according to claim 1, wherein the orthodiphenol dye comprises a benzene ring or a condensed aromatic ring carrying at least two hydroxyl groups on two consecutive carbon atoms of the ring.

11. The method according to claim 1, wherein the orthodiphenol is a compound of formula:

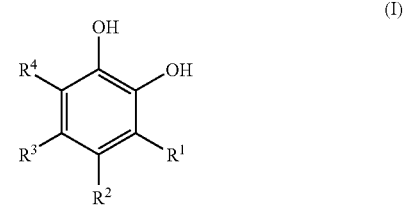

(I)

where the $R^1$ to $R_4$ substituents are identical or different and represent a hydrogen atom, a halogen, hydroxyl, carboxyl, alkyl carboxylate, optionally substituted amino, linear or branched optionally substituted alkyl, linear or branched optionally substituted alkenyl, optionally substituted cycloalkyl, alkoxy, alkoxyalkyl, alkoxyaryl, the aryl group optionally being substituted, aryl, substituted aryl and optionally substituted heterocyclic moiety, a moiety containing one or more silicon atoms, wherein two of the $R_1$ to $R_4$ substituents form together a saturated or unsaturated ring optionally containing one or more heteroatoms or optionally condensed with one or more saturated or unsaturated rings optionally containing one or more heteroatoms.

12. The method according to claim 1, wherein the oxidation dye is selected from the group consisting of flavanol, flavonols, anthocyaninidin, anthocyanin, hydroxybenzoate, flavone, iridoid, such compounds being optionally osylated and/or in the form of oligomers, optionally osylated hydroxystilbenes, 3,4-dihydroxyphenylalanine and derivates thereof, 2,3-dihydroxyphenylalanine and derivates thereof, 4,5-dihydroxyphenylalanine and derivates thereof, 4,5-dihydroxyindole and derivates thereof, 6,7-dihydroxyindole and the derivates thereof, 2,3-dihydroxyindole and derivates thereof, dihydroxycinnamates, hydroxycoumarins, hydroxyisocoumarins, hydroxycoumarones, hydroxyisocoumarones, hydroxychalcones, hydroxychromones, anthocyans, quinones, hydroxyxanthones, and mixtures thereof.

13. The method according to claim 1, wherein the oxidation dye is 5,6-dihydroxyindole or 5,6-dihydroxyindole-carboxylic acid.

14. The method according to claim 1, wherein the orthodiphenol oxidation dye is comprised within at least one extract selected from the group consisting of plant, fruit, citrus, vegetable extract, and mixtures thereof.

15. The method according to claim 1, wherein the orthodiphenol oxidation dye is comprised within at least one extract selected from the group consisting of tea, grape, apple, banana, potato extract and mixtures thereof.

16. The method according to claim 1, wherein said second oxidation dye comprises a mixture of an oxidation base and a coupling agent.

17. The method according to claim 1, wherein said second oxidation dye is an oxidation base selected from the group consisting of ortho- and para-phenylenediamine, double base, ortho-aminophenol, para-aminophenol, heterocyclic base, acid addition salt thereof, and mixtures thereof.

18. The method according to claim 1, wherein said second oxidation dye is a para-phenylenediamine of the following formula:

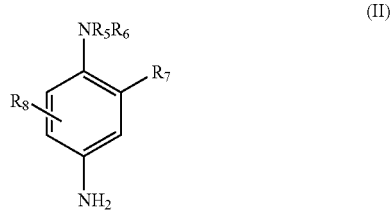

(II)

where:
$R_5$ represents a hydrogen atom, $C_1$–$C_4$ alkyl, $C_1$–$C_4$ monohydroxyalkyl, $C_2$–$C_4$ polyhydroxyalkyl, ($C_1$–$C_4$) alkoxy($C_1$–$C_4$)alkyle, nitrogen-substituted $C_1$–$C_4$ allyl, phenyl or 4'-aminophenyl moieties;
$R_6$ represents a hydrogen atom, $C_1$–$C_4$ alkyl, $C_1$–$C_4$ mono-hydroxyalkyl or $C_2$–$C_4$ polyhydroxyalkyl, ($C_1$–$C_4$)alkoxy($C_1$–$C_4$)alkyl or nitrogen-substituted $C_1$–$C_4$ alkyl moieties;
$R_7$ represents a hydrogen atom, a halogen atom, such as a chlorine atom, $C_1$–$C_4$ alkyl, sulfo, carboxy, $C_1$–$C_4$ monohydroxyalkyl or $C_1$–$C_4$ hydroxyalkoxy, $C_1$–$C_4$ acetylaminoalkoxy, $C_1$–$C_4$ mesylaminoalkoxy or $C_1$–$C_4$ carbomoylaminoalkoxy moieties;
$R_8$ represents a hydrogen, a halogen atom or a $C_1$–$C_4$ alkyl moiety;
$R_5$ and $R_6$ may also form together with the nitrogen atom carrying them a 5 or 6 ring member nitrogen heterocycle optionally substituted by one or more alkyl, hydroxy or ureido groups.

19. The method according to claim 18, wherein the paraphenylenediamine is selected from the group consisting of paraphenylenediamine, paratoluylenediamine, 2-chloro-paraphenylenediamine, 2-isopropyl-paraphenylenediamine, 2-β-hydroxyethylparaphenylenediamine, 2-β-hydroxyethyloxy-paraphenylenediamine, 2,6-dimethyl-paraphenylenediamine, 2,6-diethyl-paraphenylenediamine, 2,3-dimethyl-paraphenylene-diamine, N,N-bis-(β-hydroxyethyl)-paraphenylenediamine, 2-chloro-para-phenylenediamine, acid addition salt thereof, and mixtures thereof.

20. The method according to claim 1, wherein said second oxidation dye is a double base selected from the group consisting of double bases having the formula (III):

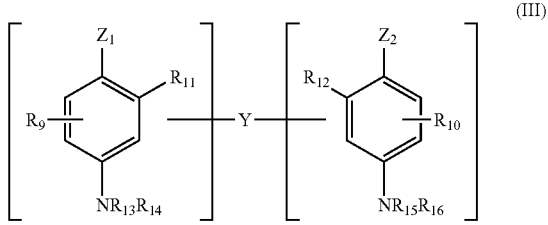

(III)

where:
$Z_1$ and $Z_2$ are identical or different and represent a hydroxyl or —$NH_2$ moiety which may be substituted by a $C_1$–$C_4$ alkyl moiety or by a linking arm Y;

the linking arm Y represents a linear or branched alkylene chain comprising from 1 to 14 carbon atoms, which may be interrupted or terminated by one or more nitrogen groups and/or by one or more heteroatoms such as oxygen, sulfur or nitrogen atoms and optionally substituted by one or more $C_1$–$C_6$ hydroxyl or alkoxy moieties;
$R_9$ and $R_{10}$ represent a hydrogen or halogen atom, $C_1$–$C_4$ alkyl, $C_1$–$C_4$ monohydroxyalkyl, $C_2$–$C_4$ polyhydroxyalkyl, $C_1$–$C_4$ aminoalkyl moieties or a linking arm Y;
$R_{11}$, $R_{12}$, $R_{13}$, $R_{14}$, $R_{15}$ and $R_{16}$ are identical or different and represent a hydrogen atom, a linking arm Y or a $C_1$–$C_4$ alkyl moiety,
provided that the compounds of the formula (III) only comprise one linking arm Y per molecule.

21. The method according to claim 20, wherein the double base is selected from the group consisting of N,N'-bis-(β-hydroxyethyl)-N,N'-bis-(4'-aminophenyl)-1,3-diamino propanol, N,N'-bis-(β-hydroxyethyl)-N,N'-bis-(4'-aminophenyl)ethylenediamine, N,N'-bis-(4-aminophenyl)tetramethylenediamine, N,N'-bis-(β-hydroxyethyl)-N,N'-bis-(4-aminophenyl)tetramethylenediamine, N,N'-bis-(4-methyl-aminophenyl)tetramethylene-diamine, N,N'-bis-(ethyl)-N, N'-bis-(4'-amino, 3'-methylphenyl)ethylene-diamine, 1,8-bis-(2,5-diaminophenoxy)-3,5-dioxaoctane, acid addition salt thereof, and mixtures thereof.

22. The method according to claim 1, wherein said second oxidation dye is an oxidation base is selected from the group consisting of one or more para-aminophenols of the formula (IV):

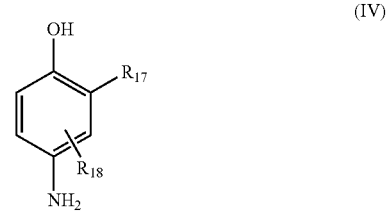

(IV)

where:
$R_{17}$ represents a hydrogen atom, a halogen atom such as fluorine or chlorine, $C_1$–$C_4$ alkyl, $C_1$–$C_4$ monohydroxyalkyl, $C_1$–$C_4$)alkoxy($C_1$–$C_4$)alkyl or $C_1$–$C_4$ aminoalkyl or ($C_1$–$C_4$)hydroxyalkyl($C_1$–$C_4$)aminoalkyl group; and
$R_{18}$ represents a hydrogen atom or a halogen atom such as fluorine or chlorine, $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alcoxy($C_1$–$C_4$)alkyl group.

23. The method according to claim 22, wherein the para-aminophenols are selected from the group consisting of para-aminophenol, 4-amino-3-methyl-phenol, 4-amino-3-fluoro-phenol, 4-amino-3-hydroxymethyl-phenol, 4-amino-2-methyl-phenol, 4-amino-2-hydroxymethyl-phenol, 4-amino-2-methoxymethyl-phenol, 4-amino-2-aminomethyl-phenol, 4-amino-2-(β-hydroxyethyl-aminomethyl)-phenol, acid addition salt thereof, and mixtures thereof.

24. The method according to claim 1, wherein said second oxidation dye is an orthoaminophenol selected from the group consisting of 2-amino-phenol, 2-amino-1-hydroxy-5-methyl-benzene, 2-amino-1-hydroxy-6-methyl-benzene, 5-acetamido-2-amino-phenol, acid addition salt thereof, and mixtures thereof.

25. The method according to claim 1, wherein said second oxidation dye is a heterocyclic base selected from the group consisting of pyridine derivate, pyrimidine derivate, pyrazole derivate, acid addition salt thereof, and mixtures thereof.

26. The method according to claim 25, wherein the pyridine derivate is selected from the group consisting of 2,5-diamino-pyridine, 2-(4-methoxyphenyl)amino-3-amino-pyridine, 2,3-diamino-6-methoxy-pyridine, 2-(β-methoxyethyl)amino-3-amino-6-methoxypyridine, 3,4-diamino-pyridine, and mixtures thereof.

27. The method according to claim 25, wherein the pyrimidine derivate is selected from the group consisting of 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, pyrazolo-pyrimidine derivate, pyrazolo-[1,5-a]-pyrimidine-3,7-diamine, 2,5-dimethyl-pyrazolo-[1,5]-pyrimidine-3,7-diamine; 2,5-dimethyl-pyrazolo-[1,5-a]-pyrimidine-3,7-diamine, pyrazolo-[1,5-a]-pyrimidine-3,5-diamine, 2,7-dimethyl-pyrazolo-[1,5-a]-pyrimidine-3,5-diamine, 3-amino-pyrazolo-[1,5-a]-pyrimidin-7-ol, 3-amino-pyrazolo-[1,5-a]-pyrimidin-5-ol, 2-(3-amino-pyrazolo-[1,5-a]-pyrimidin-7-ylamino)-ethanol, 2-(7-amino-pyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo[1,5-a]pyrimidin-3-yl)-(2-hydroxy-ethyl)-amino]-ethanol, 5,6-dimethyl-pyrazolo-[1,5-a]-pyrimidine-3,7-diamine, 2,6-dimethyl-pyrazolo-[1,5-a]-pyrimidine-3,7-diamine, 2,5,N7,N7-tetramethyl-pyrazolo-1[1,5-a]-pyrimidine-3,7-diamine, 3-amino-5-methyl-7-imidazolylpropylamino-pyrazolo-[1,5-a]-pyrimidine, acid addition salt thereof, tautomers thereof, and mixtures thereof.

28. The method according to claim 25, wherein the pyrazole derivate is selected from the group consisting of 4,5-diamino-1-methyl-pyrazole, 3,4-diamino-pyrazole, 4,5-diamino-1-(4'chlorobenzyl)-pyrazole, 4,5-diamino 1,3-dimethyl-pyrazole, 4,5-diamino-3-methyl-1-phenyl-pyrazole, 4,5-diamino-1-methyl-3-phenyl-pyrazole, 4-amino-1,3-dimethyl-5-hydrazino-pyrazole, 1-benzyl-4,5-diamino-3-methyl-pyrazole, 4,5-diamino-3-tert-butyl-1-methyl-pyrazole, 4,5-diamino-1-tert-butyl-3-methyl-pyrazole, 4,5-diamino-1-(β-hydroxyethyl)-3-methyl-pyrazole, 4,5-diamino-1-(β-hydroxy-ethyl)-pyrazole, 4,5-diamino-1-ethyl-3-methyl-pyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methyl-pyrazole, 4,5-diamino-3-hydroxymethyl-1-isopropyl-pyrazole, 4,5-diamino-3-methyl-1-isopropyl-pyrazole, 4-amino-5-(2'-aminoethyl)amino-1,3-dimethyl-pyrazole, 3,4,5-triamino-pyrazole, 1-methyl-3,4,5-triamino-pyrazole, 3,5-diamino-1-methyl-4-methylamino-pyrazole and 3,5-diamino-4-(β-hydroxy-ethyl)amino-1-methyl-pyrazole, and mixtures thereof.

29. The method according to claim 1, wherein the oxidation dye is present in an amount of 0.0005 to 12% by weight based on the total weight of the composition.

30. The method according to claim 1, wherein said second oxidation dye is a coupling agent selected from the group consisting of meta-aminophenol, meta-phenylenediamine, metadiphenol, naphthol, heterocyclic coupling agent, indolic derivate, indolinic derivate, sesamol, sesamol derivate, pyridinic derivate, pyrazolotriazole derivate, pyrazolone, indazole, benzimidazole, benzothiazole, benzoxazole, 1,3-benzodioxole, quinoline, acid addition salt thereof, and mixtures thereof.

31. The method according to claim 1, wherein said second oxidation dye is a coupling agent selected from the group consisting of 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis-(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindolin, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo-[3,2-c]-1,2,4-triazole, 2,6-dimethyl-pyrazolo-[1,5-b]-1,2,4-triazole, acid addition salt thereof, and mixtures thereof.

32. The method according to claim 1, wherein said second oxidation dye comprises a coupling agent in an amount ranging from 0.0001 to 15% by weight of the total weight of the composition.

33. The method according to claim 1, wherein the composition further comprises an amino acid, a protein, or mixtures thereof.

34. The method according to claim 1, wherein the composition further comprises at least one thiol-group containing amino acid which has an amine function in an α-position relative to a carboxylic acid function.

35. The method according to claim 33, which comprises an amino acid and wherein the amino acid is selected from the group consisting of cysteine, cysteine derivate, and mixtures thereof; and the protein is selected from the group consisting of glutathione, glutathione derivate, and mixtures thereof.

36. The method according to claim 1, wherein the composition further comprises at least one amino acid and at least one protein, wherein a molar ratio of the amino acid and protein to the oxidation dye ranges from 0.001 to 50.

37. A method of reducing transcutaneous passage of an oxidation dye of a composition, comprising:
 a physiologically acceptable medium, at least one enzyme, and
 at least one orthodiphenol oxidation dye, wherein the method comprises adding to the composition, a catalytic system comprising at least one first component selected from the group consisting of Mn(II) salt, Mn(II) oxide, Zn(II) salt, Zn(II) oxide, and combinations thereof,
 and at least one second component selected from the group consisting of alkaline hydrogencarbonate, alkaline earth hydrogencarbonate, and mixtures thereof,
 wherein at least one of the following equations are satisfied:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

where [Mn(II)], [Zn(II)] and [HCO$_3$] respectively represent the molar concentrations of Mn(II), Zn(II) and HCO$_3$ in the composition.

38. The method according to claim 37, wherein the at least one enzyme is selected from the group consisting of pyranose oxidase, glucose oxidase, glycerol oxidase, lactate oxidase, pyruvate oxidase, uricase, choline oxidase, sarcosine oxidase, bilirubin oxidase, laccase, tyrosinase, peroxydase, catalase, superoxid dimutase, enzyme-containing vegetable extract, enzyme-containing animal extract, and mixtures thereof.

39. The method according to claim 38, wherein the the at least one enzyme is tyrosinase.

40. The method according to claim 1, wherein the at least one enzyme is present in an amount ranging from $5 \times 10^{-3}$ to 5 mg enzyme per mL of the composition.

41. The method according to claim 1, wherein the orthodiphenol oxidation dye is present in an amount of 1 mM to 10 mM per liter of the composition.

42. The method according to claim 1, wherein the physiologically acceptable medium is a solubilizing medium for the oxidation dye.

43. The method according to claim 1, wherein the physiologically acceptable medium comprises a solvent or a mixture of solvents of the dye.

44. The method according to claim 1, wherein the physiologically acceptable medium is a solvent selected from the group consisting of water, alcohol, ether, dimethylsulfoxide, N-methylpyrrolidone, acetone and mixtures thereof.

45. The method according to claim 1, wherein the physiologically acceptable medium is an alcohol selected from the group consisting of alkanol, alkanediol, and mixtures thereof.

46. The method according to claim 1, wherein the physiologically acceptable medium is a water/alcohol mixture.

47. The method according to claim 1, wherein the physiologically acceptable medium is a water/alcohol mixture wherein the alcohol is present in an amount up to 80% by weight of the mixture.

48. The method according to claim 1, wherein the composition is free from any chelatant of the Mn(II) and/or Zn(II) salts.

* * * * *